United States Patent
Lopath et al.

(10) Patent No.: US 7,189,229 B2
(45) Date of Patent: Mar. 13, 2007

(54) BALLOON ALIGNMENT AND COLLAPSING SYSTEM

(75) Inventors: Patrick David Lopath, Stamford, CT (US); Edward Paul Harhen, Duxbury, MA (US); Yegor Sinelnikov, Port Jefferson, NY (US); James D. Savage, Port Jefferson Station, NY (US); Jaime Merino, Elmont, NY (US); John Hotmer, Selden, NY (US)

(73) Assignee: ProRhythm, Inc., Setauket, NY (US)

( * ) Notice: Subject to any disclaimer, the term of this patent is extended or adjusted under 35 U.S.C. 154(b) by 451 days.

(21) Appl. No.: 10/635,170

(22) Filed: Aug. 6, 2003

(65) Prior Publication Data

US 2004/0068257 A1   Apr. 8, 2004

Related U.S. Application Data

(63) Continuation-in-part of application No. 10/244,271, filed on Sep. 16, 2002, now Pat. No. 6,808,524.

(51) Int. Cl.
*A61B 18/04* (2006.01)

(52) U.S. Cl. .......................... 606/27; 606/194
(58) Field of Classification Search ............ 606/27–52, 606/191, 194, 198
See application file for complete search history.

(56) References Cited

U.S. PATENT DOCUMENTS

| | | | |
|---|---|---|---|
| 4,338,942 A | 7/1982 | Fogarty | |
| 4,402,307 A | 9/1983 | Hanson et al. | |
| 4,403,612 A | 9/1983 | Fogarty | |
| 4,813,934 A | 3/1989 | Engelson et al. | |
| 5,338,295 A | 8/1994 | Cornelius et al. | |
| 5,492,532 A | 2/1996 | Ryan et al. | |
| 5,643,279 A | 7/1997 | Trotta | |
| 5,669,932 A | 9/1997 | Fischell et al. | |
| 5,776,141 A | 7/1998 | Klein et al. | |
| 5,800,392 A | 9/1998 | Racchini | |
| 5,868,708 A | 2/1999 | Hart et al. | |
| 5,868,779 A | 2/1999 | Ruiz | |
| 6,011,995 A | 1/2000 | Guglielmi et al. | |
| 6,096,054 A | 8/2000 | Wyzgala et al. | |
| 6,102,908 A | 8/2000 | Tu et al. | |
| 6,183,492 B1 | 2/2001 | Hart et al. | |
| 6,355,051 B1 | 3/2002 | Sisskind et al. | |
| 6,589,274 B2 | 7/2003 | Stiger et al. | |
| 6,607,476 B1 | 8/2003 | Barnhart | |
| 6,626,861 B1 | 9/2003 | Hart et al. | |
| 2002/0065512 A1 | 5/2002 | Fjield et al. | |

*Primary Examiner*—Roy D. Gibson
*Assistant Examiner*—Pete Vrettakos
(74) *Attorney, Agent, or Firm*—Lerner, David, Littenberg, Krumholz & Mentlik, LLP

(57) ABSTRACT

A balloon catheter is provided with a sleeve and a flexible material where, upon inflation of the balloon, the sleeve is slid over a ball joint, preventing the flexible material and tube from moving through a range of motion in order to prevent the tube from kinking and misaligning.

46 Claims, 6 Drawing Sheets

BALLOON ALIGNMENT AND COLLAPSING SYSTEM

CROSS-REFERENCE TO RELATED APPLICATIONS

The present application is a continuation-in-part of U.S. patent application Ser. No. 10/244,271, filed Sep. 16, 2002, the disclosure of which is now U.S. Pat. No. 6,808,524 incorporated by reference herein.

BACKGROUND OF THE INVENTION

The present invention relates to apparatus incorporating balloons and to techniques employing balloons.

Certain medical and veterinary procedures employ balloons mounted on catheters for various purposes. For example, as described in co-pending, commonly-assigned U.S. patent application Ser. No. 09/905,227, published as U.S. Pat. No. 2002/0065512-A1, the disclosures of which are hereby incorporated by reference herein, a structure including a balloon is used as a reflector for directing ultrasonic energy from an ultrasonic transducer mounted within the balloon onto a region of tissue to be ablated. As further described in the aforementioned application, the balloon structure also focuses the ultrasonic energy. Such a device can be used, for example, to ablate cardiac tissue in treatment of cardiac arrhythmias. Other balloon structures are used for other medical and veterinary procedures.

Typically, the balloon is placed within the body of the subject by threading a carrier catheter having the balloon attached thereto into the body of the subject through the vascular system or other passages within the body and into the desired treatment location with the balloon in a deflated condition. Once the balloon is at the desired location within the subject's body, the balloon is inflated, the desired procedure is performed and the balloon is again deflated and withdrawn by withdrawing the carrier catheter. In many procedures, it is desirable to maintain alignment between portions of the balloon, and to maintain alignment between features of the balloon and the carrier catheter while the balloon is in an inflated condition. For example, in certain preferred embodiments taught in the aforementioned '227 application, the ultrasonic transducer is mounted on a portion of the carrier catheter disposed within the balloon adjacent a proximal end of the balloon. The ultrasonic transducer is generally cylindrical and is coaxial with the carrier catheter. When the balloon is in an inflated condition, the proximal to distal, or lengthwise, axis of the balloon should also be coaxial with the transducer for optimum focusing of the ultrasonic energy.

It would be desirable to provide a rigid reinforcing element which extends between the carrier catheter or ultrasonic transducer and the distal end of the balloon, so as to prevent tilting of the balloon or deformation of the balloon in radial directions, transverse to the lengthwise or proximal to distal direction of the carrier catheter and transducer. However, it is also necessary to allow some flexibility of the balloon in the radial directions when the balloon is deflated to allow threading of the catheter during insertion and withdrawal. The balloon must bend in the radial directions to follow the curves of the vascular system or other body passages.

Some devices which employ balloons also require a passage through the balloon. For example, in many procedures, the threading operation relies on a guide wire which is threaded through the lumen of the carrier catheter and out through the distal end of the structure into the vascular system. After the guide wire is threaded, the catheter, with the balloon thereon, is advanced along the guide wire. In other situations, it may be desirable to introduce structures such as sensing electrodes or other instruments, anchoring elements or the like through the lumen of the catheter and advance these structures so that they project beyond the distal end of the balloon.

Ordinarily, the proximal end of the balloon is affixed to the carrier catheter. As further explained below, the balloon tends to expand in radial directions transverse to the lengthwise direction and to contract in the lengthwise direction when inflated. Thus, the distal end of the balloon should be free to move relative to the carrier catheter in the lengthwise direction during inflation and deflation. Simply providing an extension of the carrier catheter projecting distally through the balloon and through the wall of the balloon at the distal end will not allow for such movement unless a sliding seal is provided at the juncture of the carrier catheter and the distal end. Such a sliding seal increases the bulk of the assembly in the deflated condition and introduces significant reliability issues. Thus, there exists a need for a better structure to provide a lumen or bore extending through the interior of the balloon.

SUMMARY OF THE INVENTION

Apparatus according to one aspect of the present invention includes a balloon having proximal and distal ends and a lengthwise direction between the ends. The balloon has a deflated length between its ends in the deflated condition and an inflated length in an inflated condition, the inflated length being less than the deflated length. Apparatus according to this aspect of the invention also includes a plurality of engagement elements disposed at least partially within the balloon. These elements are moveable with respect to one another in the lengthwise direction. As the balloon contracts in the lengthwise direction upon inflation, the balloon urges the engagement elements into engagement with one another. However, the engagement elements are moveable away from one another in the lengthwise direction upon deflation of the balloon.

Most preferably, apparatus according to this aspect of the invention also includes a carrier catheter having a lumen. An end of the balloon, most preferably the proximal end of the balloon, is secured to the carrier catheter. The engagement elements may include a fixed engagement element secured to the carrier catheter and disposed within the balloon adjacent the proximal end thereof. The engagement elements desirably include a movable engagement element which engages the fixed engagement when the balloon is in its inflated condition. Apparatus according to this aspect of the invention allows the balloon to flex in directions transverse to the lengthwise direction of the carrier catheter while the balloon is deflated and while the engagement elements are disengaged from one another. However, when the balloon is inflated, the engagement elements are forced into engagement with one another so as to provide a rigid support extending lengthwise within the balloon. The support limits or prevents deflection of the distal end of the balloon in the radial directions relative to the proximal end of the balloon and relative to the carrier catheter, thereby maintaining the balloon in alignment with the carrier catheter. The engagement elements may be arranged to abut one another axially when engaged with one another. In another arrangement, the engagement elements telescopically engage one another when engaged with one another. The exterior diameter of one element fits closely within an interior bore of the adjacent element, so that the elements are held in precise coaxial alignment with one another when in the engaged condition, thereby holding the ends of the balloon in precise alignment with one another when the balloon is inflated.

Apparatus according to this aspect of the invention may include an axial member extending in the lengthwise direction within the balloon. The axial member most desirably is a flexible member and desirably includes a spring as, for example, a coil spring, and the spring acts to urge the proximal and distal ends of the balloon away from one another when the balloon is deflated. For example, the engagement elements may be small tubular elements surrounding a coil spring. Alternatively or additionally, one or more of the engagement elements may bear a stem projecting axially from such engagement element. The stem remains disposed in the next adjacent engagement element when the engagement elements are disengaged from one another. The stem allows the engagement elements to pivot relative to one another. For example, a stem on one engagement element may include a bulbous, desirably spherical, tip which remains engaged in the interior bore of another engagement element.

The axial member within the balloon may incorporate a tube. Desirably, the tube is distensible in the lengthwise direction. A proximal end of the tube is mechanically linked to the proximal end of the balloon. For example, the proximal end of the tube may be mechanically connected to the carrier catheter or to the stop, so that the interior bore of the tube communicates with the lumen of the carrier catheter. The distal end of the tube is mechanically linked to the distal end of the balloon. Thus, when the balloon is deflated, the tube is stretched in the lengthwise direction. When the balloon is inflated, the tube is shortened in the lengthwise direction. The tube cooperates with the lumen of the catheter so as to provide a continuous passage extending through the lumen of the catheter and out through the distal end of the balloon. Most preferably, the tube is formed from material as, for example, an expanded polymer, so that the diameter or radial dimensions of the interior bore do not decrease substantially when the tube is stretched in the lengthwise direction. Thus, the continuous passage remains fully functional in all conditions of the balloon. This facilitates use of the assembly with guide wires or other instruments which must protrude beyond the distal end of the balloon.

These and other objects, features and advantages of the present invention will be more readily apparent from the detailed description of the preferred embodiments, set forth below, taken in conjunction with the accompanying drawings.

DETAILED DESCRIPTION

Figure 1:
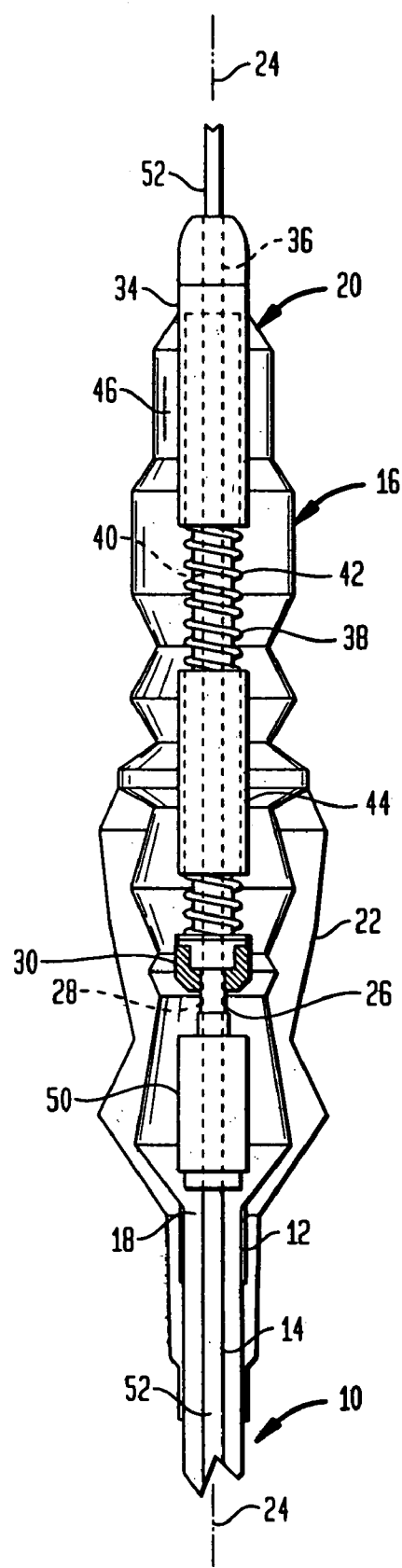
FIG. 1 is a diagrammatic, partially sectional view of a device in accordance with one embodiment of the invention.

Apparatus in accordance with one embodiment of the present invention includes a carrier catheter 10 having a distal end 12 and a proximal end (not shown) remote from the distal end. Ordinarily, the proximal end of the carrier catheter is intended to remain outside of the body, or otherwise accessible to the position for manipulation during the procedure, whereas the distal end is intended to be inserted into the body. Carrier catheter 10 has a central lumen 14. A balloon 16 has a proximal end 18 attached to the distal end of the carrier catheter and has a distal end 20 remote from the proximal end. Balloon 16 is shown in an arbitrary, wrinkled shape representing the balloon in a deflated condition. Balloon 16 desirably is formed from a film which is flexible, but which can form a substantially non-compliant balloon structure when inflated. As explained in the '227 application, materials such as those used to form non-compliant balloons in the angioplasty art such as thin films of polymers such as PET, PETG, nylon, polyurethane and polyethylene can be used. The balloon may be designed for an inflation pressure on the order of a few pounds per square inch to about 12 pounds per square inch or more, most preferably about 8 pounds per square inch, and the balloon wall desirably has the minimum thickness required to withstand the design inflation pressure without rupture as, for example, about 0.001 inches or less and preferably 0.0005 inches or less. Balloon 16 desirably is arranged to form a predetermined shape in the inflated condition (FIG. 2) as, for example, a surface of revolution about a central axis 24 coincident with the central axis of carrier catheter 10 at the distal end 12 thereof, i.e., a generally vertical axis seen in FIG. 1.

An auxiliary balloon 22 surrounds balloon 16 adjacent the proximal end thereof. The auxiliary balloon may be formed from materials similar to those used in the main balloon 16. The central lumen 14 of the carrier catheter, or another lumen (not shown), communicates with the interior of main balloon 16, whereas a different lumen within the carrier catheter (not shown) communicates with the interior of auxiliary balloon 22 so that these balloons may be inflated with different fluids as, for example, an aqueous fluid in the main balloon and air or another gas in the auxiliary balloon. The differences in acoustic impedance between these fluids cause the interface between the main and auxiliary balloons to be highly reflective to ultrasound when the balloons are so inflated.

A rigid, tubular extension 26 is fastened to the distal end of the carrier catheter and extends coaxially with the carrier catheter and with axis 24. Extension 26 has an interior bore 28 continuous with the central lumen 14 of the carrier catheter. A fixed engagement element or stop 30 surrounds the exterior of extension 26 at the distal end of the extension, remote from the carrier catheter within main balloon 16. A hollow, cylindrical nosepiece 34 having an interior bore 36 open at the distal end of the nosepiece (the upper end seen in FIG. 1) is attached to the distal end 20 of the balloon. Nosepiece 34 may be formed from a substantially rigid material as, for example, a metal. The balloon wall may be fastened to the nosepiece by an adhesive (not shown).

A flexible, distensible tube 38 having an interior bore 40 extends between stop 30 and nosepiece 34. The proximal end of the tube is fastened to the stop 30 and, hence, to extension 26, carrier catheter 10 and the proximal end 12 of the balloon, whereas the distal end of the tube is fastened to the nosepiece. The interior bore 40 of tube 38 communicates with the bore 36 in the nosepiece and with the bore 28 within extension 26, 50 that the extension 26, tube 40 and nosepiece 36 cooperatively define a continuous passage communicating with the central bore 14 of the carrier catheter and extending through the interior of balloon 16, this passable opening to the exterior of the main balloon 16 at the distal end 20 of the main balloon. Tube 38 desirably is formed from a material such as an expanded polymer as, for example, expanded polytetraflourethylene ("PTFE") or expanded polyethylene. Where the expanded polymer itself is porous, the tube may have a very thin covering of a deformable, nonporous material such as an elastomer. Expanded PTFE tubes sold by Impra, Inc., a subsidiary of C. R. Bard, Inc., of Tempe, Ariz., USA, and commonly employed as a vascular graft material may be employed. Tubes formed from the preferred materials have the property that the interior bore of the tube does not substantially contract in radial directions, transverse to the lengthwise direction along the axis of the tube, when the tube is stretched in the lengthwise direction. Although the present invention is not limited by any theory of operation, it is believed that this property results from the low Poisson's ratio of the material constituting the tube wall. Desirably, when the tube is stretched to the elongated state depicted in FIG. 1, with the balloon fully deflated, the interior diameter of the tube does not vary by more than about 20 percent of the nominal interior diameter, i.e., the diameter of the tube in an axially-shortened, fully inflated condition as depicted in FIG. 2. Most typically, the tube and the interior bore are circular in cross-section. Thus, the diameter of the interior bore is simply the dimension of the interior bore in any direction transverse to the axial direction of the tube. If the tube has a non-circular cross-section, the diameter of the interior bore can be considered as the largest dimension in any direction transverse to the axial direction. Typically, the interior bore has a nominal diameter of about 0.8–1.2 mm and does not vary by more than about 0.2 mm as the tube is stretched throughout the normal operating range, from the fully inflated condition to the fully deflated condition. Further, tubes formed from the preferred expanded polymer materials tend to resist collapse when subjected to external pressure. The most preferred materials, such as expanded PTFE, also have a low coefficient of friction which further facilitates passage of guidewires and other elements through the tube. Moreover, as further discussed below, the tube is stretched by the action of a coil spring during operation of the device. The preferred materials offer very low resistance to stretching.

In one embodiment the tube is formed from expanded PTFE, has a nominal interior diameter of 0.038 inches (0.97 mm) in the unstretched condition, and when stretched by about 30–35% of its unstretched length, has an interior diameter sufficient to pass a guide wire of 0.035 inches (0.89 mm) diameter. In the unstretched condition, even when subjected to an external pressure of 8 pounds per square inch, the tube will pass the same guide wire.

A cylindrical coil spring 42 surrounds tube 38 and extends between stop 30 and nosepiece 34. The ends of the spring are secured to stop 30 and nosepiece 34. The coil spring is generally cylindrical and is coaxial with tube 38. Thus, the coil spring 42 and tube 38 form a composite axial member extending generally in the lengthwise direction within main balloon 16. In one embodiment, spring 42, in its relaxed condition, is about 28–30 mm long.

A first or proximal mobile engagement element 44 in the form of a thin-walled, hollow cylinder surrounds coil spring 42 and tube 38. In the deflated condition of main balloon 16 illustrated in FIG. 1, the proximal engagement element 44 is slideable on the coil spring and can move proximally and distally from the position shown. A second or distal mobile engagement element 46 surrounds the coil spring 42 and tube 38 at and adjacent the distal end 20 of main balloon 16. The distal engagement element 46 is a hollow, tubular structure. The distal engagement element may be formed integrally with nosepiece 34 or may be bonded to the nosepiece. Engagement elements 44 and 46 are formed from substantially rigid materials as, for example, from metallic materials such as stainless steel tubing. In one embodiment, the engagement elements have an outside diameter of 0.125 inches (3.175 mm) and an inside diameter of 0.105 inches (2.667 mm).

A cylindrical, generally tubular ultrasonic transducer 50 encircles the extension 26 between the stop 30 and the proximal end 18 of the main balloon, so that the ultrasonic transducer is disposed within the main balloon.

Figure 2:
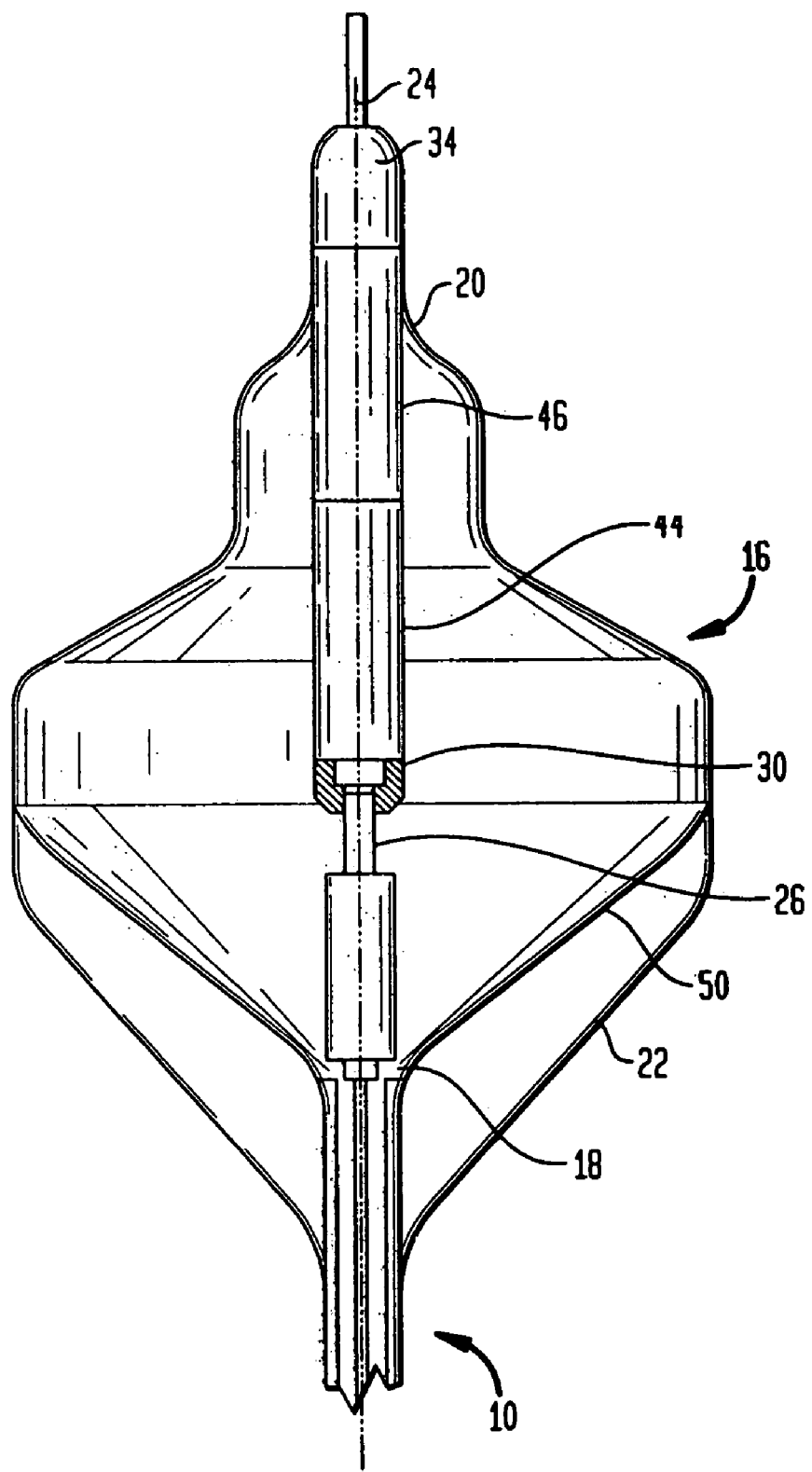
FIG. 2 is a fragmentary, diagrammatic view similar to FIG. 1 showing the device in an inflated condition.

In operation, the assembly is initially provided with the balloons deflated, so that the assembly is substantially in the condition depicted in FIG. 1. In this deflated condition, spring 42 is in a relaxed condition, whereas the balloons are in a twisted condition. An elongated element such as a guide wire 52 is threaded through the central lumen 14 of the carrier catheter through the bore 28 of extension 26, through the bore 40 of tube 38 and through the nosepiece bore 36, so that the guide wire projects beyond the distal end 20 of the main balloon 16. Using conventional techniques, the guide wire is threaded into the subject as, for example, through the vascular system of the subject. Once the guide wire is in place, the carrier catheter with the balloons thereon is advanced along the guide wire and through the vascular system. During threading, the balloon assembly is substantially free to flex in radial directions, transverse to the lengthwise direction and transverse to axis 24. Because the mobile engagement elements 44 and 46 are disengaged from one another and remote from one another, at least that portion of spring 42 and tube 38 disposed in the gap between the mobile engagement elements can flex readily. Likewise, that portion of the spring and tube disposed between the proximal mobile engagement element 44 and the fixed engagement element or stop 30 can also flex.

Once the distal end of the catheter has been advanced to or near the desired location within the subject, the balloons are inflated as depicted in FIG. 2. Upon inflation, the main balloon 16 expands in radial direction, but contracts in the lengthwise or axial direction, so that the distal end 20 of the main balloon moves towards the proximal end 18 and towards the carrier catheter 10. The balloon untwists as it inflates, and hence the distal end of the balloon rotates, relative to the proximal end of the balloon, about the central axis 24. This motion compresses and twists spring 42 (FIG. 1) and shortens tube 38 in the lengthwise direction. In one embodiment, spring 42 is compressed by about 9 mm, i.e., to about 68 percent of its free length, and twisted through a full rotation (360 degrees) about central axis 24. The motion of the balloon ends towards one another also urges the mobile engagement elements 46 and 44 axially towards one another and urges the proximal mobile engagement element 44 into engagement with the fixed engagement element or stop 30, so that the assembly reaches the condition depicted in FIG. 2. The forces exerted by the balloon on the engagement elements can be substantial. In one typical embodiment, with a balloon in the inflated condition and in the configuration depicted in FIG. 2, about six pounds force is applied axially to hold the engagement elements in engagement with one another. In the inflated condition, the engagement elements are engaged with one another so that they abut one another and provide a substantially rigid column.

The rigid column formed by the engagement elements extends between the rigid extension 26 of the carrier catheter and nosepiece 34. Thus, the distal end of the column is mechanically linked to the distal end of the balloon, whereas the proximal end of the column is mechanically linked to the proximal end 18 of the balloon through extension 26. The column, thus, holds the nosepiece and the distal end 20 of the balloon in alignment with the axis 24 of the carrier catheter. This maintains alignment of the main balloon 16 with the ultrasonic transducer 50 and provides the optimum focusing action. While the assembly is in this condition, the guide wire 52 may be left in place or may be withdrawn and replaced with another elongated probe, catheter or guide wire. For example, a sensing device may be advanced through the bores to measure physiological conditions in the region distal to the balloon.

Ultrasonic energy may be applied by transducer 50 to ablate tissue surrounding the central axis 24 as, for example, to ablate a ring-like lesion in the wall of the heart as described more fully in the '227 application.

After completion of the desired treatment, the balloons are deflated. The spring 42 (FIG. 1) forces the proximal and distal ends of the balloons away from one another, thereby facilitating radial contraction of the balloon and returning the assembly substantially to the state illustrated in FIG. 1. In this process, the engagement elements return to the disengaged condition depicted in FIG. 1. The spring also returns to its relaxed, untwisted condition, so that the twisting motion about axis 24 imparted to the spring during inflation is reversed. Thus, the distal end of the spring and hence nosepiece 34 and the distal end 20 of the balloon rotate relative to the proximal end of the spring about axis 24, thereby twisting the balloon around axis 24 and restoring it to substantially the original deflated condition. The axial and twisting motions aid in collapsing the balloon to a compact state. The carrier catheter and balloons are then withdrawn from the subject.

Numerous variations and combinations of the features described above can be utilized without departing from the present invention as defined by the claims. For example, the arrangement of engagement elements can be employed in structures which omit the tube 38 and which consequently omit the function of the tube in providing a passageway through the balloon. In such an arrangement, the engagement elements are guided by the spring alone, or by another flexible member provided in place of the spring. Also, the tube 38 can be formed from an ordinary material such as, for example, an elastomer or the like, which contracts or "necks" in the radial directions to a substantial extent when the tube is extended. Such an assembly is less preferred, inasmuch as the interior bore of the tube would partially or fully close when the assembly is in the deflated condition. Conversely, the preferred tubes, as discussed above, can be employed even in structures which do not incorporate the engagement elements. Also, the invention can be employed in balloon structures which do not utilize a catheter connected to the proximal end of the balloon.

The number of engagement elements can be varied. Apparatus according to a further embodiment of the invention (FIG. 3) is similar to the apparatus discussed above with reference to FIGS. 1 and 2 except that the two mobile engagement elements discussed above are replaced by a single mobile engagement element 144 which is fixed to the nosepiece 134 and hence to the distal end of the balloon. This mobile engagement element is a tubular structure similar to the mobile engagement elements discussed above, and surrounds the spring 142 and tube 138. In the deflated condition shown in FIG. 3, the proximal end of mobile engagement element 144 is remote from the fixed engagement element or stop 130. Thus, the assembly is free to flex in directions transverse to axis 124 in the gap 102 between the engagement elements. This flexibility facilitates threading of the assembly through the vascular system and removal of the assembly after treatment, in a manner similar to that discussed above. In the inflated condition, the proximal end of mobile engagement element 144 abuts the fixed engagement element or stop 130 to provide a column or support as discussed above. The assembly according to this embodiment, however, is more resistant to kinking in the deflated condition, during threading and removal.

The tubular mobile engagement element 144 is provided with one or more holes 145 extending through the wall of the tube. Holes 145 facilitate purging of air from the small space within the bore of the engagement element, immediately surrounding tube 138, when balloon 116 is filled with a liquid. Similar holes may be provided in the mobile engagement elements shown in FIGS. 1 and 2.

For example, proximal engagement element 44 can be replaced by two shorter engagement elements. Also, the proximal mobile engagement element 44 discussed above can be fixed to the fixed engagement element or stop 30.

In a further variant, where ultrasonic transducer 50 is not required or is located in a different region, stop 30 can be omitted so that the proximal mobile engagement element abuts directly against the distal end of the catheter at the proximal end of the balloon. As discussed above, the engagement elements cooperate with the spring to limit deformation of the spring to localized areas of the spring at joints between the elements when the balloon is in an inflated condition. This effect will provide at least some increased rigidity even if the engagement elements do not abut one another, but merely approach one another in the inflated condition of the balloon.

Figure 4:
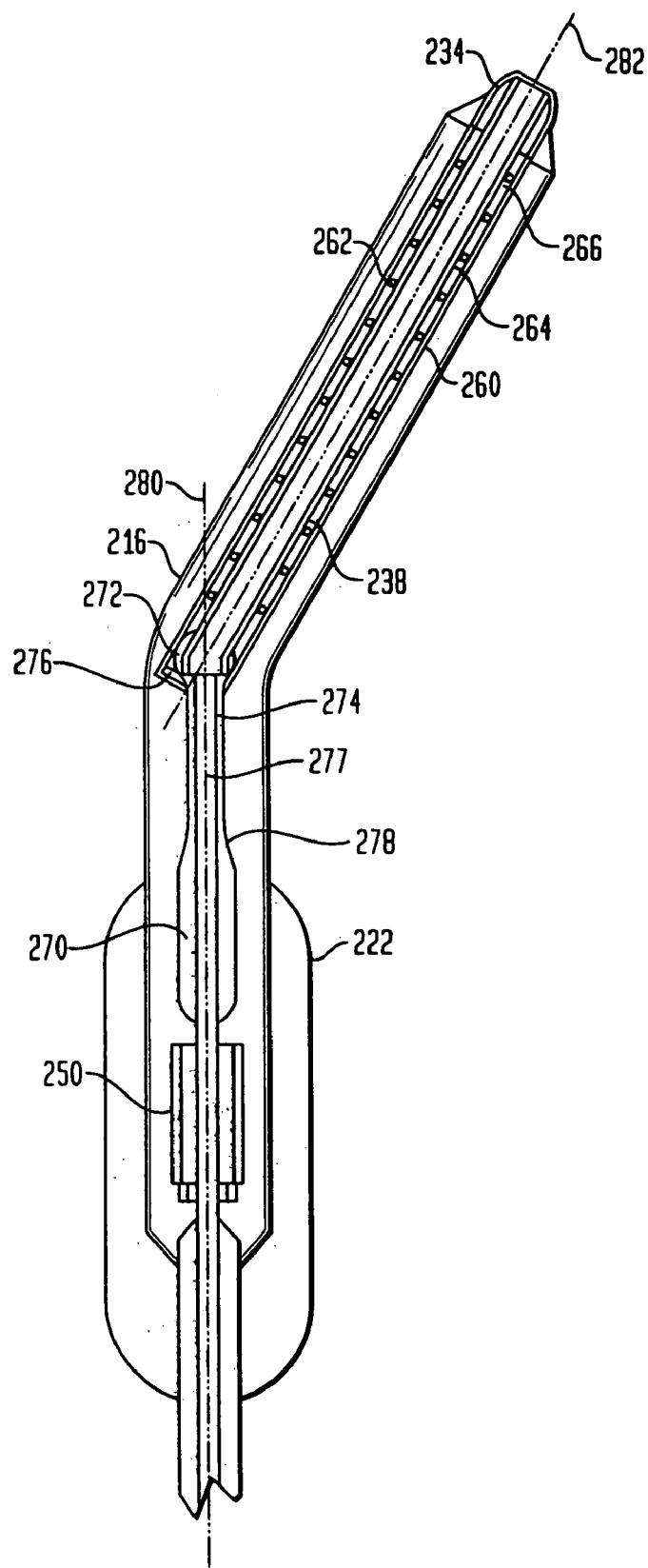
FIG. 4 is a diagrammatic, partially sectional view of a device according to a further embodiment of the invention.
Figure 5:
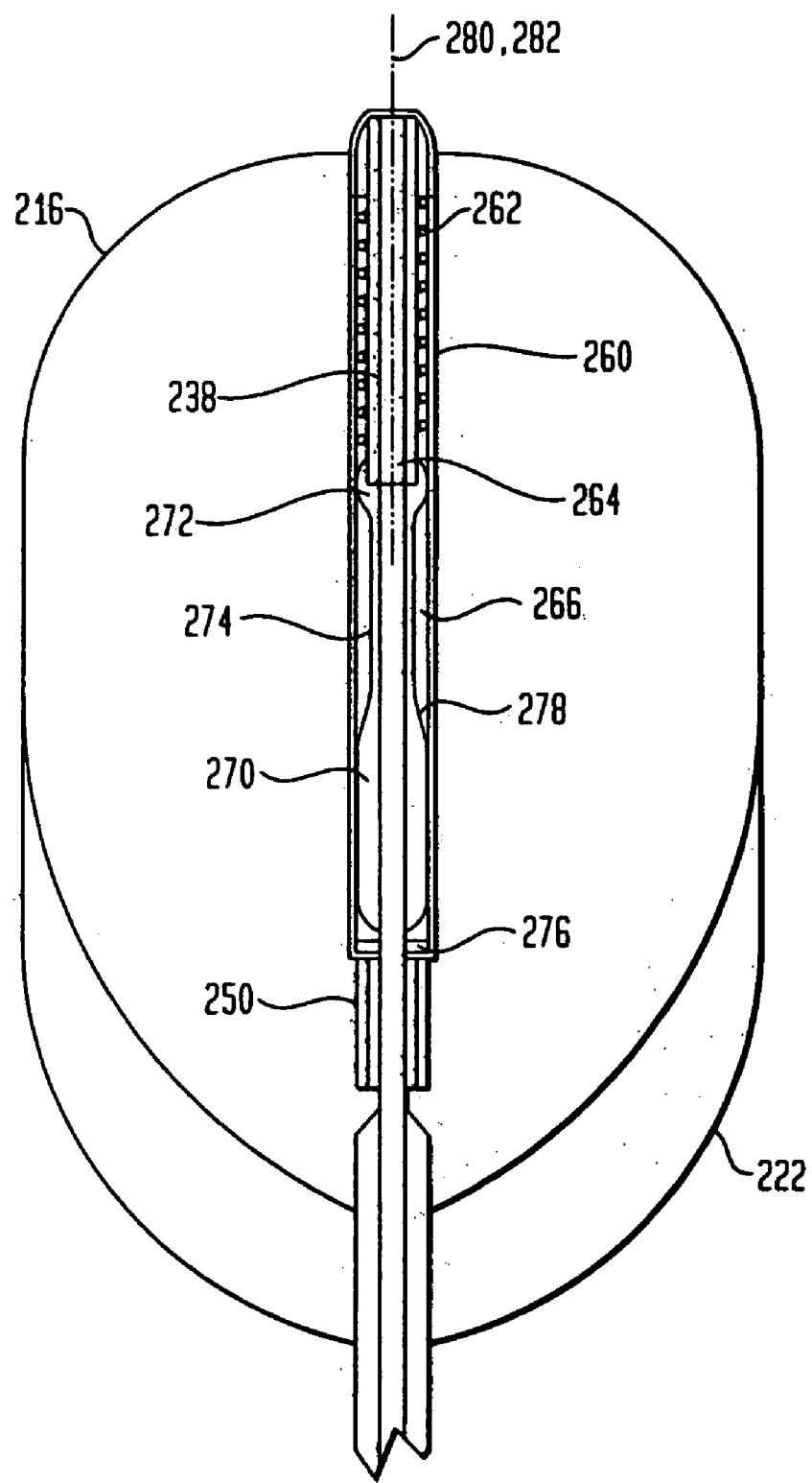
FIG. 5 is a fragmentary, diagrammatic view similar to FIG. 4 showing the device in an inflated condition.

Apparatus according to another embodiment includes a first engagement element 270 and a second engagement element 260 (FIGS. 4 and 5). As in the embodiments discussed above, the engagement elements 260, 270 are located within the balloon 216. The first engagement element 270, also referred to herein as a "male" engagement element, is generally in the form of a cylinder having an axis 280. The first engagement element is mounted to catheter 210 just distal to an ultrasonic transducer 250, as by a rigid tubular extension 226 of the catheter, so that the first engagement element is in fixed position relative to the transducer and relative to the proximal end 218 of the balloon. The axis 280 of the first engagement element 270 is coincident with the central axis of transducer 250 and with the central axis of the catheter. A stem 274 projects from the distal end of the first engagement element 270 along axis 280. The stem is fixed to the first engagement element and desirably is formed integrally with the first engagement element from a substantially rigid material such as a metal. The stem includes a main portion 275, which is generally in the form of a body of revolution about axis 280, such as a cylinder or cone. At least that part of main portion 275 remote from the first engagement element 270 has a diameter smaller than the diameter of the first engagement element, and hence has a smaller cross-sectional area than the first engagement element 270. The first engagement element 270 has a tapered surface 278 leading to the stem 274. The diameter of surface 274 decreases progressively in the distal direction, between the cylindrical portion of the first engagement element and the stem. The stem 274 includes a bulbous tip 272 remote from the first engagement element 270 and distal to the main portion 275. The bulbous tip 272 is wider than the main portion of the stem 274. That is, the bulbous tip has maximum dimensions transverse to axis 280 greater than the corresponding dimensions of stem 274. The bulbous tip 272 has an exterior surface, referred to herein as the ball joint surface, in the form of a zone of a sphere having its center on axis 280. The diameter of the ball joint surface is larger than the diameter of stem main portion 275, and equal to or just slightly less than the diameter of first engagement element 270. The first engagement element 270 and stem 274 cooperatively define a bore 277 extending along axis 280 from the proximal end of the first engagement element to the distal end of the stem, at bulbous element 272.

The second engagement element 260, also referred to as a "female" engagement element, is a hollow tube defining an axis 282 and a cylindrical interior bore 266. The second engagement element has a distal end fastened to the distal end of balloon 216 by a nosepiece 234. The second engagement element 260 most preferably is formed from a substantially rigid material such as a metal, except that a portion of the second engagement element, at the proximal end of the element, is formed from a relatively soft material such as a polymer or a sleeve of soft material is placed over the proximal portion of the second engagement element.

The interior bore 266 of the second engagement element has an interior diameter just slightly larger than the external diameter of first engagement element 270, and just slightly larger than the diameter of bulbous element 272. For example, the internal diameter of bore 266 may exceed the diameter of first engagement element 270 by about 0.001–0.004 inches (25–100 μm) so that the second engagement element defines a free-running fit with the first engagement element. Also, the internal diameter of bore 266 preferably exceeds the exterior diameter of bulbous tip 272 by about 0.001–0.004 inches (25–100 μm). Bore 266 is open at its proximal end.

Within the second engagement element 260 is flexible, distensible tube 238 similar to the flexible tubes discussed above. Tube 238 extends between the distal end of stem 274 and nosepiece 234. The tube defines an interior bore 239 communicating with the interior bore 277 of the stem and first engagement element, and with the lumen of catheter 210. Bore 239 communicates with the exterior of the balloon through nosepiece 234, at the distal end of the balloon. A helical spring 262 is also disposed within bore 266 of the second engagement element. Spring 262 surrounds tube 238. The spring bears on the distal end of stem 274, at bulbous portion 272, and on nosepiece 234, so that the spring urges the engagement elements 260, 270 and the ends of the balloon 216 away from one another.

When the balloon 216 is in its deflated condition, the engagement elements 260, 270 are in the disengaged position illustrated in FIG. 4. The bulbous portion or ball joint surface 272 of the stem lies inside bore 266, adjacent the open proximal end of the bore. In this condition, the engagement elements 260 and 270 are pivotable relative to one another so that the axis 282 of the second engagement element can pivot relative to the axis 280 of the first engagement element through a predetermined angular range in any direction about the center of the spherical ball joint surface 272. As the second engagement element 260 pivots about the bulbous tip 272, the flexible material 238 and spring 266 can bend. The pivoting motion allows the balloon to flex in directions transverse to the catheter 210. This flexibility helps the catheter track over guide wires and maneuver through the anatomy during placement of the device in the patient and during removal from the patient. However, second engagement element 260 is substantially constrained by the stem, and particularly by the ball joint surface of bulbous portion 272, against translational movement relative to the first engagement element in directions transverse to the axis 280 of the first engagement element. This assures that the balloon 216, the tube 238 and spring 266 cannot kink. In the deflated condition, the proximal end of the second engagement element 260 may bear on the interior of balloon 216, particularly when the assembly is bent as shown in FIG. 4. However, the soft material 276 constituting the proximal end of the second engagement element 260 does not tend to cut or tear the balloon.

FIG. 5 shows the assembly with the balloon in its inflated state. As the balloon 216 inflates, the length of the balloon decreases and compresses the spring 262. As the spring 262 is compressed, the second engagement element 260 moves toward the first engagement element 270. In this motion, the stem 274 moves deeper into bore 266 of the second engagement element. The progressive engagement of the stem in the bore will force the second engagement element into alignment with the first engagement element. This process continues as the proximal end of the first engagement element encounters the tapered guide surface 278 and then the first engagement element 270. In the fully inflated condition of FIG. 5, with the second engagement element 260 telescopically encompassing the first engagement element 270, the close fit between the exterior of the first engagement element and the interior of the second engagement element assures that the engagement elements are coaxial with one another, so that axis 282 is coincident with axis 280. The distal end of the balloon is held precisely coaxial with the proximal end of the balloon, and hence coaxial with the transducer 250 and with the reflective parabolic interface region defined by balloon 216 and auxiliary balloon 222. Upon deflation, spring 262 forces the second engagement element away from the first engagement element, and thus stretches the balloon 216 axially, restoring the assembly to the flexible condition depicted in FIG. 4. The engagement elements disengage one another up to the point of where the second engagement element 260 still encompasses the bulbous tip 272 of stem 274. In this embodiment, the spring may or may not twist the balloon during deflation to assist in orderly collapse of the balloon as discussed above.

The arrangement of FIGS. 4 and 5 can be varied. For example, the positions of the engagement elements can be reversed, so that the male or stem-bearing first engagement element 270 is mounted to the distal end of the balloon and the tubular or female engagement element 260 is mounted to the proximal end of the balloon and to the catheter. Also, the assembly can include more than two engagement elements. For example, the assembly may include two tubular, female engagement elements and a male engagement element disposed between them, so that the two female engagement elements approach the male element from opposite sides during inflation. In such an embodiment, the male engagement element may have two stems projecting in opposite directions so that one stem projects into each female element.

Figure 6:
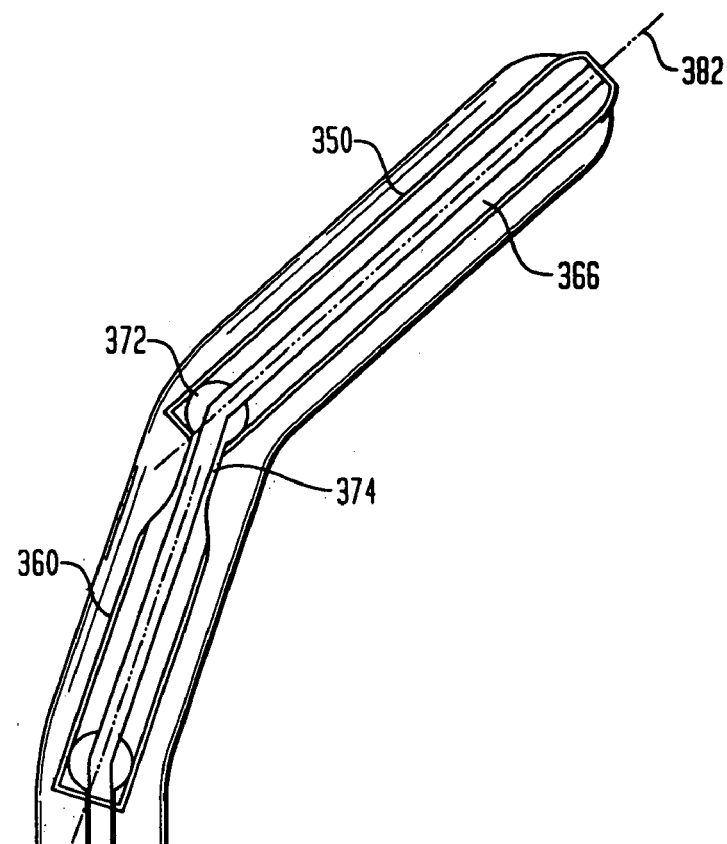
FIG. 6 is a diagrammatic, partially sectional view of a device according to a further embodiment of the invention.

Apparatus according to another embodiment includes a third engagement element 350 (FIG. 6). The third engagement element 350 is also referred to as a "female" engagement element as it is a hollow tube defining an axis 382 and a cylindrical interior bore 366. The third engagement element has a similar structure to that described above with reference to FIGS. 4 and 5 for the second engagement element 260, while the second middle engagement element 360 has a proximal end resembling that of the previously described second engagement element 260 and a distal end resembling that of the previously described first engagement element. Thus, a stem 374 projects from the distal end of the second or middle engagement element, such stem having a bulbous element 372. Here again, the engagement elements desirably are formed from substantially rigid materials, except that the second engagement element 360 and the third engagement element 350 each have a relatively soft material such as a polymer at their respective proximal ends to prevent damage to the balloon caused by engagement between the balloon and the proximal ends of these elements in the deflated condition. In the deflated condition illustrated, the engagement elements are free to pivot relative to one another about the bulbous tips of the stems in the same manner as discussed above with reference to FIGS. 4 and 5. In the inflated condition, the third engagement element 350 telescopically receives the exterior of the second engagement element 360 and the second engagement element telescopically receives the exterior of the first engagement element 370. Here again, the engaged elements are constrained in coaxial relationship with one another, thereby keeping the proximal and distal ends of the balloon in precise alignment with one another, and in precise alignment with internal structures such as a transducer 301, when the balloon is in the inflated condition.

The structure of FIG. 6, with three engagement elements, provides increased flexibility in the deflated condition as compared to an otherwise equivalent structure with two engagement elements. Further variants can include additional engagement elements to further increase flexibility in the deflated condition.

Figure 3:
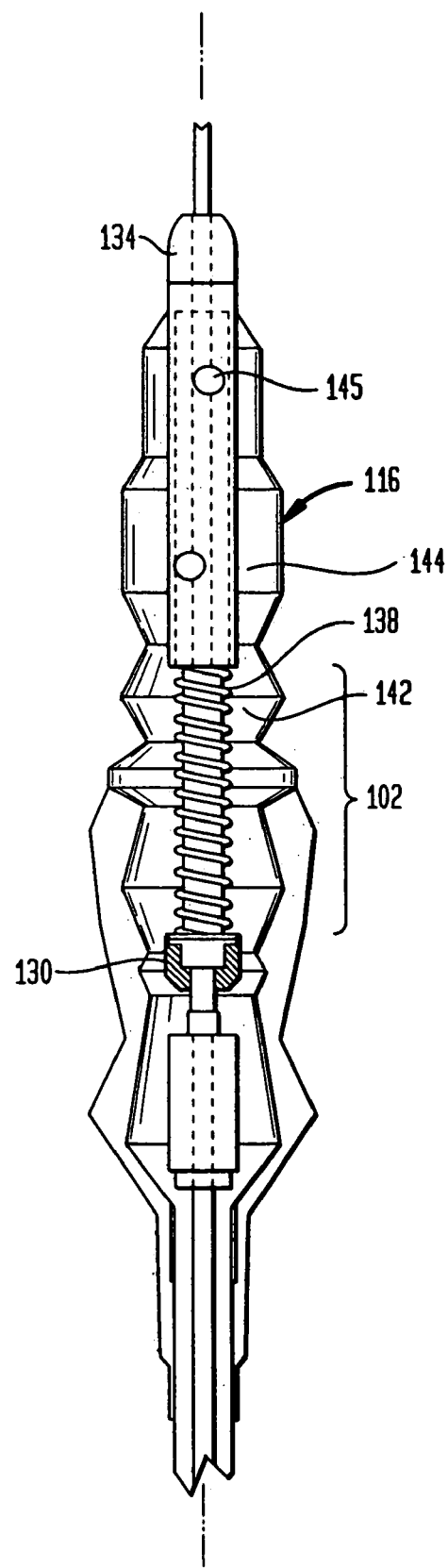
FIG. 3 is a view similar to FIG. 1 depicting a device according to a further embodiment of the invention.

The stem arrangement discussed above with reference to FIGS. 4 and 5 can be used where the engagement elements abut one another in the inflated condition of the balloon, as in FIGS. 1–3, rather than encompassing one another telescopically. In a further variant, the first engagement element 270 of FIGS. 4 and 5 can be provided with a shoulder at or near its proximal end, so that the proximal end of the second engagement element will abut such shoulder in the inflated condition of the balloon. Engagement elements that encompass one another as shown in FIGS. 4–6 can be employed without the stem. Also, the stem can be modified to include a bulbous portion in the form of a disc or other non-spherical surface, or to omit the bulbous portion entirely. If the bulbous portion is omitted, the anti-kinking function typically will be less effective. Further it is not essential that the first engagement element have a smooth, cylindrical surface. For example, first engagement element 270 may have an exterior surface defined by a set of ribs, fins or other projections.

Figure 7:
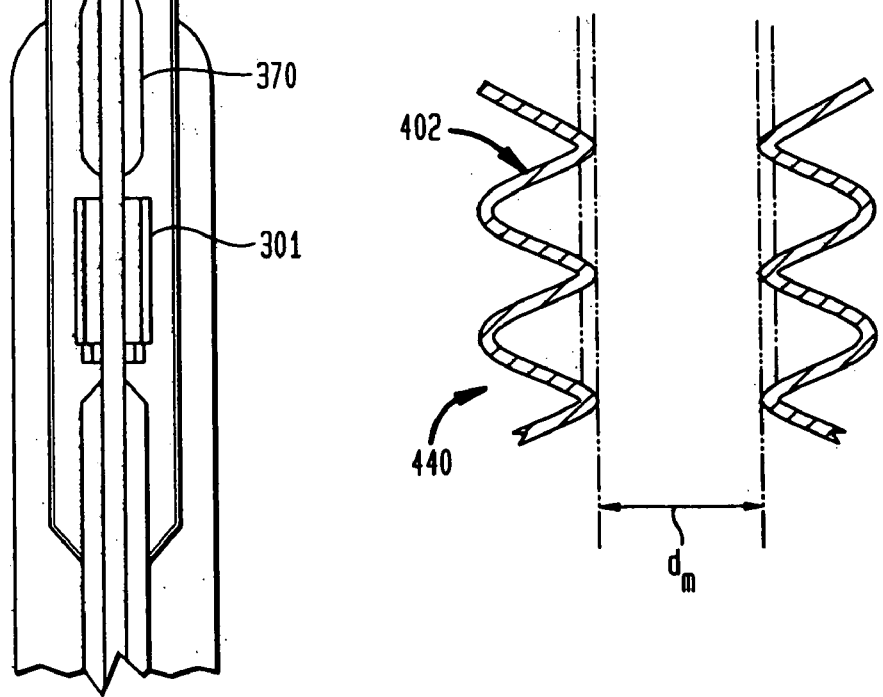
FIG. 7 is a fragmentary, diagrammatic sectional view of a tube used in a further embodiment of the invention.

In a variant, the tube 40 discussed above with reference to FIGS. 1 and 2 may have a convoluted shape as seen in FIG. 7. Thus, the tube 440 may be generally in the form of a small bellows having convolutions such that the convolutions define a minor diameter $d_M$. Such a tube can stretch axially (upwardly and downwardly as seen in FIG. 7) from the axially-contracted condition shown in solid lines to the axially-extended condition shown in broken lines. In effect, the convolutions are partially or fully extended. Desirably, the minor diameter $d_M$ does not decrease substantially during extension. Such a tube can be made of the materials discussed above, or from other materials such as conventional polymers and elastomers.

As these and other variations and combinations of the features described above can be utilized without departing from the present invention, the foregoing description of the preferred embodiments should be taken by way of illustration rather than by limitation of the invention as defined by the claims.

What is claimed is:

1. Apparatus comprising:
   (a) a balloon having proximal and distal ends and a lengthwise direction between said ends, said balloon having an inflated condition and a deflated condition, said balloon having a deflated length between said ends in the deflated condition and an inflated length in the inflated condition, said inflated length being less than said deflated length, and
   (b) a plurality of engagement elements disposed at least partially within said balloon and movable with respect to one another in the lengthwise direction, said balloon urging said engagement elements into engagement with one another upon inflation of the balloon, said engagement elements being movable away from one another in the lengthwise direction upon deflation of the balloon, and
   wherein said plurality of engagement elements includes a first engagement element and a second engagement element, said second engagement element at least partially telescopically encompassing said first engagement element when said balloon is in said inflated condition.

2. Apparatus as claimed in claim 1, wherein said plurality of engagement elements includes a third engagement element, said third engagement element at least partially telescopically encompassing said second engagement element when said balloon is in said inflated condition.

3. Apparatus as claimed in claim 1, wherein said first engagement element defines an axis, said second engagement element defines an axis, said engagement elements are pivotable relative to one another so that the axis of the second engagement element can pivot relative to the axis of the first engagement element through a predetermined angular range when said balloon is in said deflated condition.

4. Apparatus as claimed in claim 3, wherein said second engagement element is substantially constrained against translational movement relative to said first engagement element in directions transverse to the axis of the first engagement element when said balloon is in said deflated condition.

5. Apparatus as claimed in claim 1, further comprising a stem projecting from said first engagement element, said stem being disposed inside said second engagement element when said balloon is in said deflated condition, at least a part of said stem having a smaller cross-sectional area than said first engagement element.

6. Apparatus as claimed in claim 5, wherein said first engagement element has a tapered surface leading into said stem.

7. Apparatus as claimed in claim 6 wherein the end portion of said second engagement element can pivot about said bulbous tip.

8. Apparatus as claimed in claim 5, wherein said stem includes a bulbous tip remote from said first engagement element and a main portion connecting said bulbous tip to said first engagement portion, said bulbous tip being wider than said main portion, said bulbous tip being disposed inside said second engagement element when said balloon is in said deflated condition.

9. Apparatus as claimed in claim 8 wherein said bulbous tip defines a balljoint surface in the form of a zone of a sphere, said balljoint surface having a diameter.

10. Apparatus as claimed in claim 9 wherein said first engagement element and said stem cooperatively define a stem bore extending along the axis from the proximal end of said first engagement element to the distal end of said stem at said bulbous tip.

11. Apparatus as claimed in claim 9 wherein said second engagement element has an interior bore, said interior bore having an internal diameter larger than the diameter of said ball-joint surface.

12. Apparatus as claimed in claim 11 wherein said internal diameter is about 25–100 microns larger than said diameter of said ball-joint surface.

13. Apparatus as claimed in claim 9, further comprising a flexible tube within said second engagement element, wherein said flexible tube can flex when said balloon is in a deflated state.

14. Apparatus as claimed in claim 13 wherein said flexible material is substantially coaxial with said second engagement element.

15. Apparatus as claimed in claim 13, wherein said spring surrounds said flexible material.

16. Apparatus as claimed in claim 5, further comprising a spring disposed within said second engagement element, said spring urging said engagement elements and said ends of said balloon away from one another when said balloon is deflated.

17. Apparatus as claimed in claim 16, wherein said spring is compressed when said balloon is in said inflated state.

18. Apparatus as claimed in claim 1 wherein said first engagement element has an outside diameter and said second engagement element has a interior bore which encompasses said first engagement element when said balloon is in said inflated condition, said interior bore having an internal diameter slightly larger than the outside diameter of said first engagement element so that said first and second engagement elements are constrained in substantially coaxial alignment with one another when said balloon is in said inflated condition.

19. Apparatus as claimed in claim 18, wherein said internal diameter of said interior bore in said second engagment element is about 25–100 microns larger than said outside diameter of said first engagement element.

20. Apparatus as claimed in claim 1, wherein an end portion of said second engagement element closest to said first engagement element includes a soft material to prevent said balloon from being damaged.

21. Apparatus as claimed in claim 19, wherein said second engagement element includes a substantially rigid tube and a sleeve of said soft material at said end portion of said second engagement element closest to said first engagement element.

22. Apparatus as claimed in claim 1, wherein said first engagement element is located proximally to said second engagement element and said second engagement element is located distally from said first engagement element.

23. Apparatus as claimed in claim 1, wherein one engagement element completely telescopically encompasses another engagement element when said balloon is in said inflated condition.

24. Apparatus as claimed in claim 1 further comprising an axial member extending in the lengthwise direction within the balloon, said axial member at least partially constraining said engagement elements in radial directions transverse to said lengthwise direction.

25. Apparatus as claimed in claim 24 wherein said axial member has a proximal end mechanically linked to the proximal end of the balloon and a distal end mechanically linked to the distal end of the balloon.

26. Apparatus as claimed in claim 25 wherein said axial member includes a spring, said spring urging said ends of said balloon away from one another when said balloon is deflated.

27. Apparatus as claimed in claim 26 wherein said spring is a coil spring having an axis extending in the lengthwise direction.

28. Apparatus as claimed in claim 27 wherein at least one of said engagement elements is generally tubular and surrounds said coil spring.

29. Apparatus as claimed in claim 27 wherein said axial member further includes a tube coaxial with said coil spring and disposed within said coil spring, said tube defining an interior bore.

30. Apparatus as claimed in claim 29 further comprising a carrier catheter having a lumen, said proximal end of said balloon being secured to said carrier catheter, said lumen communicating with said interior bore of said tube.

31. Apparatus as claimed in claim 30 wherein said lumen, said stem bore and said flexible tube communicate with one another to form a continuous channel within said carrier catheter.

32. Apparatus as claimed in claim 30 wherein said plurality of engagement elements include a stop secured to said carrier catheter within said balloon adjacent the proximal end thereof and a first mobile engagement element, said first mobile engagement element engaging said stop when said balloon is in said inflated condition.

33. Apparatus as claimed in claim 32 wherein said first mobile engagement element is movable in the lengthwise direction relative to said stop and said carrier catheter when said balloon is in said deflated condition.

34. Apparatus as claimed in claim 33 wherein said first mobile engagement element is mounted to the distal end of the balloon.

35. Apparatus as claimed in claim 33 wherein said engagement elements include a second mobile engagement element mounted to the distal end of the balloon and movable in the lengthwise direction relative to said first mobile engagement element and relative to said stop, said first mobile engagement element being disposed between said second mobile engagement element and said stop.

36. Apparatus as claimed in claim 32 further comprising an ultrasonic transducer mounted to said carrier catheter within said balloon and between the proximal end of the balloon and said stop.

37. Apparatus as claimed in claim 1 wherein said plurality of engagement elements form a structure which substantially reinforces said balloon against lateral displacement when said balloon is in said inflated condition and said engagement elements are engaged with one another, said plurality of engagement elements permitting flexing of said balloon in lateral directions transverse to said lengthwise direction when said balloon is in said deflated condition.

38. A method of placing and operating a device comprising:
  (a) threading a carrier catheter into the body of a mammalian subject while a balloon secured to the carrier catheter is in a deflated condition and while engagement elements disposed at least partially within the balloon are disengaged from one another; then
  (b) inflating the balloon so that the balloon expands in radial directions and contracts in a lengthwise direction, and so that contraction of the balloon moves the engagement elements into proximity with one another;

(c) performing a procedure using the balloon in its inflated condition, said engagement elements reinforcing the balloon during said procedure; and then (d) deflating the balloon so that said engagement elements disengage from one another and withdrawing the carrier catheter and balloon while said engagement elements are disengaged from one another; and (e) urging a distal end of the balloon away from a proximal end of the balloon in a lengthwise direction during said deflating step; and wherein adjacent ones of said engagement elements are telescopically engaged in one another when said balloon is in an inflated condition, and wherein said engagement elements are constrained in coaxial alignment with one another when said balloon is inflated.

39. A method as claimed in claim 38, one of said engagement elements being connected to the proximal end of the balloon, another one of said engagement elements being connected to the distal end of the balloon, said engagement elements holding said proximal and distal ends of the balloon in alignment with one another when the balloon is inflated.

40. A method as claimed in claim 38 wherein a stem projecting from a first one of said engagement elements is disposed within a second one of said engagement elements when said balloon is in said deflated condition during said threading step, said stem allowing said second engagement element to pivot relative to said first engagement element during said threading step.

41. A method as claimed in claim 40 wherein said stem projecting from said first engagement element remains disposed within said second engagement element during said deflating and withdrawing step.

42. A method as claimed in claim 38 wherein said step of urging the distal end of the balloon is performed by a spring disposed within the balloon.

43. A method as claimed in claim 42 wherein said spring twists the distal end of the balloon relative to the proximal end during the deflating step.

44. A method as claimed in claim 38 further comprising the step of providing a guide element extending through the carrier catheter, extending through a tube disposed within the balloon and extending beyond the balloon, stretching the tube upon movement of the distal end of the balloon away from the proximal end and foreshortening the tube upon inflation of the balloon.

45. A method as claimed in claim 38 wherein said step of performing a procedure includes directing energy from a transducer disposed within the balloon to a wall of the balloon and reflecting the energy towards a target region of the subject at the wall of the balloon.

46. A method as claimed in claim 38 wherein, when said balloon is in said inflated condition said engagement elements substantially reinforce said balloon against displacement in lateral direction transverse to said lengthwise direction, and said engagement elements allow flexing of said balloon in said lateral directions when said balloon is in said deflated condition.

* * * * *

UNITED STATES PATENT AND TRADEMARK OFFICE
CERTIFICATE OF CORRECTION

| | | |
|---|---|---|
| PATENT NO. | : 7,189,229 B2 | Page 1 of 1 |
| APPLICATION NO. | : 10/635170 | |
| DATED | : March 13, 2007 | |
| INVENTOR(S) | : Patrick David Lopath et al. | |

It is certified that error appears in the above-identified patent and that said Letters Patent is hereby corrected as shown below:

Column 1, lines 9-10, "the disclosure of which is now U.S. Pat. No. 6,808,524 incorporated by reference herein." should read -- now U.S. Pat. No. 6,808,524, the disclosure of which is incorporated by reference herein. --
Column 13, line 2, "a balljoint surface" should read -- a ball-joint surface --.
Column 13, line 3, "said balljoint surface" should read -- said ball-joint surface --.

Signed and Sealed this

Twenty-sixth Day of February, 2008

JON W. DUDAS
*Director of the United States Patent and Trademark Office*